(12) United States Patent
Huang et al.

(10) Patent No.: US 7,067,302 B2
(45) Date of Patent: Jun. 27, 2006

(54) **DNA AND AMINO ACID SEQUENCE OF A TYROSINE AMMONIA LYASE ENZYME FROM THE BACTERIUM *RHODOBACTER SPHAEROIDES***

(75) Inventors: Lixuan Huang, Hockessin, DE (US); Zhixiong Xue, Chadds Ford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 416 days.

(21) Appl. No.: 10/621,826

(22) Filed: Jul. 17, 2003

(65) Prior Publication Data
US 2004/0059103 A1 Mar. 25, 2004

Related U.S. Application Data

(60) Provisional application No. 60/397,820, filed on Jul. 23, 2002.

(51) Int. Cl.
C12N 15/63 (2006.01)
C12N 9/88 (2006.01)
C07H 21/04 (2006.01)

(52) U.S. Cl. ................ 435/252.3; 435/232; 435/320.1; 536/23.2

(58) Field of Classification Search ............. 435/252.3, 435/320.1, 232; 536/23.2
See application file for complete search history.

(56) References Cited

U.S. PATENT DOCUMENTS

2003/0233675 A1* 12/2003 Cao et al. ................... 800/279

OTHER PUBLICATIONS

Accession No. ADN25163), is 91.6% identical to Applicants polypeptide of SEQ ID No.: 3, see the encllosed sequence search alignment.*

* cited by examiner

Primary Examiner—Tekchand Saidha

(57) ABSTRACT

A novel tyrosine ammonia lyase enzyme was identified in the bacterium *Rhodobacter sphaeroides*. This enzyme has a higher activity for tyrosine than for phenylalanine and is useful for the production of para-hydroxycinnamic acid directly from tyrosine. The gene encoding this enzyme was cloned by direct amplification using the genomic DNA and was expressed in *E. coli*.

9 Claims, 2 Drawing Sheets

Figure 1. SDS-PAGE Analysis of RsTAL Expression in E. coli.
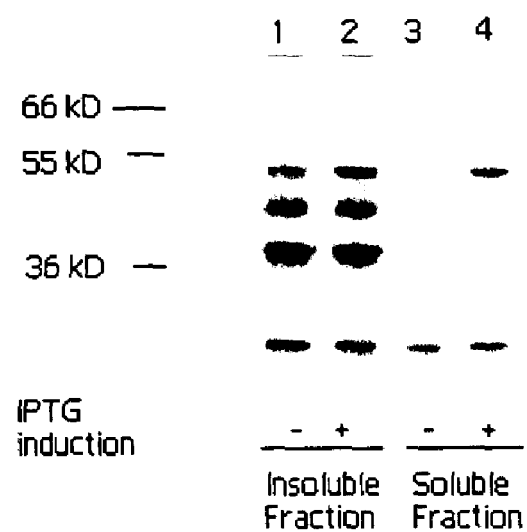

Figure 2. SDS-PAGE Analysis of the RsTAL Enzyme Purified by Anion Exchange Chromatography

SEQUENCE LISTING

```
<160> NUMBER OF SEQ ID NOS: 7

<210> SEQ ID NO 1
<211> LENGTH: 689
<212> TYPE: PRT
<213> ORGANISM: T. cutaneum

<400> SEQUENCE: 1

Met Phe Ile Glu Thr Asn Val Ala Lys Pro Ala Ser Thr Lys Ala Met
1               5                   10                  15

Asn Ala Gly Ser Ala Lys Ala Ala Pro Val Glu Pro Phe Ala Thr Tyr
                20                  25                  30

Ala His Ser Gln Ala Thr Lys Thr Val Ser Ile Asp Gly His Thr Met
            35                  40                  45

Lys Val Gly Asp Val Val Ala Val Ala Arg His Gly Ala Lys Val Glu
        50                  55                  60

Leu Ala Ala Ser Val Ala Gly Pro Val Arg Ala Ser Val Asp Phe Lys
65                  70                  75                  80
```

-continued

```
Glu Ser Lys Lys His Thr Ser Ile Tyr Gly Val Thr Thr Gly Phe Gly
                 85                  90                  95
Gly Ser Ala Asp Thr Arg Thr Ser Asp Thr Glu Ala Leu Gln Ile Ser
            100                 105                 110
Leu Leu Glu His Gln Leu Cys Gly Phe Leu Pro Thr Asp Ala Thr Tyr
        115                 120                 125
Glu Gly Met Leu Leu Ala Ala Met Pro Ile Pro Ile Val Arg Gly Ala
    130                 135                 140
Met Ala Val Arg Val Asn Ser Cys Val Arg Gly His Ser Gly Val Arg
145                 150                 155                 160
Leu Glu Val Leu Gln Ser Phe Ala Asp Phe Ile Asn Arg Gly Leu Val
                165                 170                 175
Pro Cys Val Pro Leu Arg Gly Thr Ile Ser Ala Ser Gly Asp Leu Ser
            180                 185                 190
Pro Leu Ser Tyr Ile Ala Gly Ala Ile Cys Gly His Pro Asp Val Lys
        195                 200                 205
Val Phe Asp Thr Ala Ala Ser Pro Pro Thr Val Leu Thr Ser Pro Glu
    210                 215                 220
Ala Ile Ala Lys Tyr Gly Leu Lys Thr Val Lys Leu Ala Ser Lys Glu
225                 230                 235                 240
Gly Leu Gly Leu Val Asn Gly Thr Ala Val Ser Ala Ala Ala Gly Ala
                245                 250                 255
Leu Ala Leu Tyr Asp Ala Glu Cys Leu Ala Ile Met Ser Gln Thr Asn
            260                 265                 270
Thr Val Leu Thr Val Glu Ala Leu Asp Gly His Val Gly Ser Phe Ala
        275                 280                 285
Pro Phe Ile Gln Glu Ile Arg Pro His Ala Gly Gln Ile Glu Ala Ala
    290                 295                 300
Arg Asn Ile Arg His Met Leu Gly Gly Ser Lys Leu Ala Val His Glu
305                 310                 315                 320
Glu Ser Glu Leu Leu Ala Asp Gln Asp Ala Gly Ile Leu Arg Gln Asp
                325                 330                 335
Arg Tyr Ala Leu Arg Thr Ser Ala Gln Trp Ile Gly Pro Gln Leu Glu
            340                 345                 350
Ala Leu Gly Leu Ala Arg Gln Gln Ile Glu Thr Glu Leu Asn Ser Thr
        355                 360                 365
Thr Asp Asn Pro Leu Ile Asp Val Glu Gly Gly Met Phe His His Gly
    370                 375                 380
Gly Asn Phe Gln Ala Met Ala Val Thr Ser Ala Met Asp Ser Ala Arg
385                 390                 395                 400
Ile Val Leu Gln Asn Leu Gly Lys Leu Ser Phe Ala Gln Val Thr Glu
                405                 410                 415
Leu Ile Asn Cys Glu Met Asn His Gly Leu Pro Ser Asn Leu Ala Gly
            420                 425                 430
Ser Glu Pro Ser Thr Asn Tyr His Cys Lys Gly Leu Asp Ile His Cys
        435                 440                 445
Gly Ala Tyr Cys Ala Glu Leu Gly Phe Leu Ala Asn Pro Met Ser Asn
    450                 455                 460
His Val Gln Ser Thr Glu Met His Asn Gln Ser Val Asn Ser Met Ala
465                 470                 475                 480
Phe Ala Ser Ala Arg Arg Thr Met Glu Ala Asn Glu Val Leu Ser Leu
                485                 490                 495
```

-continued

| | | | | | | | | | | | |
|---|---|---|---|---|---|---|---|---|---|---|---|
|Leu|Leu|Gly|Ser|Gln|Met|Tyr|Cys|Ala|Thr|Gln|Ala|Leu|Asp|Leu|Arg|
| | | |500| | |505| | | |510| |

Val Met Glu Val Lys Phe Lys Met Ala Ile Val Lys Leu Leu Asn Glu
        515                 520                 525

Thr Leu Thr Lys His Phe Ala Ala Phe Leu Thr Pro Glu Gln Leu Ala
        530                 535                 540

Lys Leu Asn Thr His Ala Ala Ile Thr Leu Tyr Lys Arg Leu Asn Gln
545                 550                 555                 560

Thr Pro Ser Trp Asp Ser Ala Pro Arg Phe Glu Asp Ala Ala Lys His
            565                 570                 575

Leu Val Gly Val Ile Met Asp Ala Leu Met Val Asn Asp Asp Ile Thr
            580                 585                 590

Asp Leu Thr Asn Leu Pro Lys Trp Lys Lys Glu Phe Ala Lys Glu Ala
        595                 600                 605

Gly Asn Leu Tyr Arg Ser Ile Leu Val Ala Thr Thr Ala Asp Gly Arg
        610                 615                 620

Asn Asp Leu Glu Pro Ala Glu Tyr Leu Gly Gln Thr Arg Ala Val Tyr
625                 630                 635                 640

Glu Ala Val Arg Ser Glu Leu Gly Val Lys Val Arg Arg Gly Asp Val
            645                 650                 655

Ala Glu Gly Lys Ser Gly Lys Ser Ile Gly Ser Ser Val Ala Lys Ile
        660                 665                 670

Val Glu Ala Met Arg Asp Gly Arg Leu Met Gly Ala Val Gly Lys Met
        675                 680                 685

Phe

<210> SEQ ID NO 2
<211> LENGTH: 1850
<212> TYPE: DNA
<213> ORGANISM: R. sphaeroides

<400> SEQUENCE: 2

```
ccgaggcggc catccacgag atggcggccc gtttcggcct gacgcccgcg gatctctcgc    60
tcgatctggg cccgctgggg cggacgatct gaagcaagaa actctgcatt aaccagcttc   120
cactaccttc ggcgagaaga cagggagtga agccaatgct cgccatgagc ccccgaagc   180
cggccgtcga gctggatcgc cacatcgatc tggaccaggc ccatgccgtg gcgagcggcg   240
gcgcgcggat tgtccttgcc cctccggcgc gcgaccggtg ccgtgcgtcc gaagcgcggc   300
tcggcgctgt catccgcgag gcgcgccatg tctacggact gacaaccggc ttcggtcccc   360
ttgcgaaccg cctgatctca ggtgagaatg tccgaacgct gcaggccaat cttgtccatc   420
atctggccag cggcgtggga ccggtgcttg actggacgac ggcgcgcgcc atggttctgg   480
cgcgtctggt gtcgatcgct cagggagcct ccggtgccag cgagggacc atcgctcgcc   540
tgatcgacct gctcaattcc gagctcgctc ggccgttcc cagccgcggc acggtggcg   600
cgtcgggtga cctgacaccg cttgcgcata tggtgctctg cctccagggc cggggagact   660
tcctggaccg ggacgggacg cggcttgacg gcgcagaagg gctccggcgc ggacggctgc   720
aaccgctcga tctctcccat cgcgatgcac tggcgctggt caacgggacc tccgccatga   780
ccgggatcgc gctggtgaat gctcacgcct ccgccatct cggcaactgg gcggtggcgt   840
tgacggccct gcttgcggaa tgtctgagag gccggaccga ggcatgggcc gcggcactgt   900
ccgacctgcg gccgcatccc ggacagaagg acgccgcagc gaggctgcgc gcccgcgtgg   960
acggcagcgc gcgggtggtc cggcacgtca ttgccgagcg gaggctcgac gccggcgata  1020
```

-continued

```
tcgggacgga gccggaggcg gggcaggatg cctacagcct cgctgcgct ccgcaggttc    1080 tcggggcggg cttcgacacg ctcgcatggc atgaccgggt gctgacgatc gagctgaacg    1140
cggtgaccga caatccggtg tttccgcccg atggcagcgt gcccgccctg cacgggggca    1200
atttcatggg ccagcatgtg gcgctgacgt ccgatgcgct cgccacggcc gtcaccgttc    1260
tggcgggcct tgcggagcgc cagattgcac gtctgacaga tgaaaggctg aaccgtgggc    1320 tgccccctt cctccaccgg ggccccgccg ggttgaattc cggcttcatg ggcgcacagg    1380
tgacggcgac cgcgctcctg ccgagatgc gagccacggg acctgcctcg atccattcga    1440
tctccacgaa cgccgccaat caggatgtgg tctcgcttgg gaccatcgcc gcgcgcctct    1500
gccgcgagaa gatcgaccgt tgggcggaga tccttgcgat cctcgctctc tgtcttgcac    1560
aagctgcgga gctgcgctgc ggcagcggcc tagacggggt gtctcccgcg gggaagaagc    1620
tggtgcaggc cctgcgcgag cagttcccgc cgcttgagac ggaccggccc ctgggacagg    1680
aaattgccgc gcttgctacg cacctcttgc agcaatctcc cgtctgagcg cggcctcagg    1740
tcgtggcggg atccaccgtg aggcctacag cctcggcata tttgagccag gtctcgatcg    1800
acgccacgac ggcacggacc tcgatggcga tcagctcgat cccgacgagg           1850
```

<210> SEQ ID NO 3
<211> LENGTH: 526
<212> TYPE: PRT
<213> ORGANISM: R. sphaeroides

<400> SEQUENCE: 3

```
Val Lys Pro Met Leu Ala Met Ser Pro Pro Lys Pro Ala Val Glu Leu
1               5                   10                  15

Asp Arg His Ile Asp Leu Asp Gln Ala His Ala Val Ala Ser Gly Gly
            20                  25                  30

Ala Arg Ile Val Leu Ala Pro Pro Ala Arg Asp Arg Cys Arg Ala Ser
        35                  40                  45

Glu Ala Arg Leu Gly Ala Val Ile Arg Glu Ala Arg His Val Tyr Gly
    50                  55                  60

Leu Thr Thr Gly Phe Gly Pro Leu Ala Asn Arg Leu Ile Ser Gly Glu
65                  70                  75                  80

Asn Val Arg Thr Leu Gln Ala Asn Leu Val His Leu Ala Ser Gly
            85                  90                  95

Val Gly Pro Val Leu Asp Trp Thr Thr Ala Arg Ala Met Val Leu Ala
        100                 105                 110

Arg Leu Val Ser Ile Ala Gln Gly Ala Ser Gly Ala Ser Glu Gly Thr
    115                 120                 125

Ile Ala Arg Leu Ile Asp Leu Leu Asn Ser Glu Leu Ala Pro Ala Val
    130                 135                 140

Pro Ser Arg Gly Thr Val Gly Ala Ser Gly Asp Leu Thr Pro Leu Ala
145                 150                 155                 160

His Met Val Leu Cys Leu Gln Gly Arg Gly Asp Phe Leu Asp Arg Asp
                165                 170                 175

Gly Thr Arg Leu Asp Gly Ala Glu Gly Leu Arg Arg Gly Arg Leu Gln
            180                 185                 190

Pro Leu Asp Leu Ser His Arg Asp Ala Leu Ala Leu Val Asn Gly Thr
        195                 200                 205

Ser Ala Met Thr Gly Ile Ala Leu Val Asn Ala His Ala Cys Arg His
    210                 215                 220
```

-continued

Leu Gly Asn Trp Ala Val Ala Leu Thr Ala Leu Leu Ala Glu Cys Leu
225                 230                 235                 240

Arg Gly Arg Thr Glu Ala Trp Ala Ala Leu Ser Asp Leu Arg Pro
            245                 250                 255

His Pro Gly Gln Lys Asp Ala Ala Arg Leu Arg Ala Arg Val Asp
            260                 265                 270

Gly Ser Ala Arg Val Val Arg His Val Ile Ala Glu Arg Arg Leu Asp
            275                 280                 285

Ala Gly Asp Ile Gly Thr Glu Pro Glu Ala Gly Gln Asp Ala Tyr Ser
290                 295                 300

Leu Arg Cys Ala Pro Gln Val Leu Gly Ala Gly Phe Asp Thr Leu Ala
305                 310                 315                 320

Trp His Asp Arg Val Leu Thr Ile Glu Leu Asn Ala Val Thr Asp Asn
                325                 330                 335

Pro Val Phe Pro Pro Asp Gly Ser Val Pro Ala Leu His Gly Gly Asn
            340                 345                 350

Phe Met Gly Gln His Val Ala Leu Thr Ser Asp Ala Leu Ala Thr Ala
            355                 360                 365

Val Thr Val Leu Ala Gly Leu Ala Glu Arg Gln Ile Ala Arg Leu Thr
370                 375                 380

Asp Glu Arg Leu Asn Arg Gly Leu Pro Pro Phe Leu His Arg Gly Pro
385                 390                 395                 400

Ala Gly Leu Asn Ser Gly Phe Met Gly Ala Gln Val Thr Ala Thr Ala
            405                 410                 415

Leu Leu Ala Glu Met Arg Ala Thr Gly Pro Ala Ser Ile His Ser Ile
            420                 425                 430

Ser Thr Asn Ala Ala Asn Gln Asp Val Val Ser Leu Gly Thr Ile Ala
            435                 440                 445

Ala Arg Leu Cys Arg Glu Lys Ile Asp Arg Trp Ala Glu Ile Leu Ala
450                 455                 460

Ile Leu Ala Leu Cys Leu Ala Gln Ala Ala Glu Leu Arg Cys Gly Ser
465                 470                 475                 480

Gly Leu Asp Gly Val Ser Pro Ala Gly Lys Lys Leu Val Gln Ala Leu
            485                 490                 495

Arg Glu Gln Phe Pro Pro Leu Glu Thr Asp Arg Pro Leu Gly Gln Glu
            500                 505                 510

Ile Ala Ala Leu Ala Thr His Leu Leu Gln Gln Ser Pro Val
            515                 520                 525

<210> SEQ ID NO 4
<211> LENGTH: 30
<212> TYPE: DNA
<213> ORGANISM: artificial sequence
<220> FEATURE:
<223> OTHER INFORMATION: primer

<400> SEQUENCE: 4
gatccccggg gtgaagccaa tgctcgccat                              30

<210> SEQ ID NO 5
<211> LENGTH: 30
<212> TYPE: DNA
<213> ORGANISM: artificial sequence
<220> FEATURE:
<223> OTHER INFORMATION: primer

<400> SEQUENCE: 5

```
gatcaagctt cgatcgagac ctggctcaaa                              30

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
atgaagccaa tgctcgccat                                         20

<210> SEQ ID NO 7
<211> LENGTH: 24
<212> TYPE: DNA
<213> ORGANISM: artificial sequence
<220> FEATURE:
<223> OTHER INFORMATION: primer

<400> SEQUENCE: 7
caccatgaag ccaatgctcg ccat                                    24
```

DNA AND AMINO ACID SEQUENCE OF A TYROSINE AMMONIA LYASE ENZYME FROM THE BACTERIUM RHODOBACTER SPHAEROIDES

This application claims the benefit of U.S. Provisional Application No. 60/397,820, filed Jul. 23, 2002.

FIELD OF THE INVENTION

The invention relates to the field of molecular biology and microbiology. More specifically, the invention relates to the nucleotide and amino acid sequences of a novel tyrosine ammonia lyase enzyme from the bacterium *Rhodobacter sphaeroides* to be used for production of para-hydroxycinnamic acid (pHCA).

BACKGROUND OF THE INVENTION

Para-hydroxycinnamic acid (pHCA) is a high-value, aromatic chemical compound that may be used as a monomer for the production of Liquid Crystal Polymers (LCP). LCPs are polymers that exhibit an intermediate or mesophase between the glass-transition temperature and the transition temperature to the isotropic liquid or have at least one mesophase for certain ranges of concentration and temperature. The molecules in these mesophases behave like liquids and flow, but also exhibit the anisotropic properties of crystals. LCPs are used in liquid crystal displays, and in high-speed connectors and flexible circuits for electronic, telecommunication, and aerospace applications. Because of their resistance to sterilizing radiation and their high oxygen and water vapor barrier properties, LCPs are also used in medical devices, and in chemical and food packaging.

Due to its importance as a high-value, aromatic chemical compound, chemical synthesis of pHCA is known. However, chemical synthesis is expensive due to the high energy needed for synthesis and the extensive product purification required. Biological production of pHCA offers a low cost, simplified solution to the problem.

The production of pHCA by plants using the enzymes phenylalanine ammonia lyase (PAL) (EC 4.3.1.5) and a P450 enzyme is well known. Phenylalanine ammonia-lyase is widely distributed in plants (Koukol et al., *J. Biol. Chem.* 236:2692–2698 (1961)), fungi (Bandoni et al., *Phytochemistry* 7:205–207 (1968)), yeast (Ogata et al., *Agric. Biol. Chem.* 31:200–206 (1967)), and Streptomyces (Emes et al., *Can. J. Microbiology* 48:613–622 (1970)), but it has not been found in *Escherichia coli* or mammalian cells (Hanson and Havir In *The Enzymes*, 3rd ed.; Boyer, P., Ed.; Academic: New York, 1967; pp 75–167). PAL is the first enzyme of phenylpropanoid metabolism and catalyzes the removal of the (pro-3S)-hydrogen and —$NH_3^+$ from L-phenylalanine to form trans-cinnamic acid. In the presence of a P450 enzyme system, trans-cinnamic acid can be converted to para-hydroxycinnamic acid (pHCA) which serves as the common intermediate in plants for production of various secondary metabolites such as lignin and isoflavonoids. In microbes however, cinnamic acid and not pHCA acts as the precursor for secondary metabolite formation. No cinnamate hydroxylase enzyme has so far been characterized from microbial sources. The PAL enzyme in plants is thought to be a regulatory enzyme in the biosynthesis of lignin, isoflavonoids and other phenylpropanoids (Hahlbrock et al., *Annu. Rev. Plant Phys. Plant Mol. Biol.* 40:347–369 (1989)). However, in the red yeast, *Rhodotorula glutinis* (*Rhodosporidium toruloides*), this lyase degrades phenylalanine as a catabolic function and the cinnamate formed by the action of this enzyme is converted to benzoate and other cellular materials.

Genes encoding PAL are known in the art and several have been sequenced from both plant and microbial sources (see for example EP 321488 *[Rhodosporidium toruloides]*; WO 9811205 *[Eucalyptus grandis* and *Pinus radiata]*; WO 9732023 [Petunia]; JP 05153978 *[Pisum sativum]*; WO 9307279 [potato, rice]; and for example GenBank AJ010143 and X75967). The PAL genes from various sources have been over-expressed as active PAL enzymes in yeast, *Escherichia coli* and insect cell cultures (Faulkner et al., *Gene* 143:13–20 (1994); Langer et al., *Biochemistry* 36:10867–10871 (1997); McKegney et al., *Phytochemistry* 41:1259–1263 (1996)).

Some PAL genes, in addition to their ability to convert phenylalanine to cinnamate, can accept tyrosine as substrate. In such reactions the enzyme activity is designated tyrosine ammonia lyase (TAL). Conversion of tyrosine by TAL results in the direct formation of pHCA from tyrosine without the intermediacy of cinnamate. However, there has been only one, very recent report of a gene which encodes an enzyme having significantly higher TAL catalytic activity than PAL activity (Kyndt et al., *FEBS Letters* 512:240–244 (2002)). This gene was isolated from the bacterium *Rhodobacter capsulatus* and encoded an enzyme that had a TAL catalytic efficiency that was approximately 150 times higher than that for PAL. This TAL protein was reported to have a higher homology to the PAL proteins of plants (e.g., 32% identity with the PAL sequence of *Pinus taeda*), than to the PAL sequences of yeasts. All other natural PAL/TAL enzymes prefer to use phenylalanine rather than tyrosine as their substrate. The wild-type PAL/TAL enzyme from the yeast Rhodosporidium exhibits a reduced preference for phenylalanine as compared to tyrosine, having a ratio of TAL catalytic activity to PAL catalytic activity of only 0.58 (reported in Hanson and Havir, In *The Biochemistry of Plants*; Academic: New York, 1981; Vol. 7, pp 577–625). For comparison, the PAL/TAL enzymes studied in other organisms typically possess PAL/TAL ratios of 15 or greater. Sariaslani et al. (U.S. Patent Application No. 60/383232) describe an inducible TAL enzyme that was isolated from the yeast *Trichosporon cutaneum*. This enzyme had a higher TAL than PAL activity with a PAL/TAL activity ratio of 0.73.

U.S. Pat. No. 6,368,837 discloses several methods for the biological production of pHCA. These include: the incorporation of the wild type PAL from the yeast *Rhodotorula glutinis* into *E. coli* and utilizing the ability of the wild type PAL to convert tyrosine to pHCA; the incorporation of the wild type PAL from the yeast *Rhodotorula glutinis* plus the plant cytochrome P-450 and the P-450 reductase into *E. coli* to convert phenylalanine to cinnamic acid and then to pHCA; and the development of a mutant PAL/TAL gene that encoded an enzyme with enhanced TAL activity. This mutant gene was isolated by mutagenesis of the wild type Rhodosporidium toruloides PAL and encoded an enzyme with a TAL/PAL ratio of 1.7. This gene was used to produce PCHA by direct conversion of tyrosine. The development of several other mutant PAL/TAL genes that encode enzymes with enhanced TAL activity is disclosed by Tang in U.S. Pat. No. 6,521,748. TAL/PAL ratios up to 7.2 were reported from these mutant genes. However, other enzymes with higher TAL activity are required for the economical production of PCHA.

The problem to be solved therefore is to obtain a naturally occurring enzyme with higher TAL than PAL activity to be used for the direct conversion of tyrosine to pHCA and to serve as a tool for future enzyme engineering to produce more efficient TAL enzymes. Applicants have solved the stated problem by isolating an enzyme from the bacterium Rhodobacter sphaeroides that has a higher TAL catalytic activity than PAL activity.

SUMMARY OF THE INVENTION

The invention provides an isolated nucleic acid molecule encoding a tyrosine ammonia lyase enzyme, selected from the group consisting of:
  a) an isolated nucleic acid molecule encoding the amino acid sequence as set forth in SEQ ID NO:3;
  b) an isolated nucleic acid molecule that hybridizes with (a) under the following hybridization conditions: 0.1× SSC, 0.1% SDS, 65° C. and washed with 2× SSC, 0.1% SDS followed by 0.1× SSC, 0.1% SDS; or
  an isolated nucleic acid molecule that is complementary to (a) or (b).

Additionally the invention provides polypeptides encoded by the nucleic acids of the invention as well as genetic chimera and transformed host cells containing the same.

In another embodiment the invention provides a method of obtaining a nucleic acid molecule encoding a tyrosine ammonia lyase enzyme comprising:
  a) probing a genomic library with the nucleic acid molecule of the invention;
  b) identifying a DNA clone that hybridizes with the nucleic acid molecule of the invention; and
  c) sequencing the genomic fragment that comprises the clone identified in step (b), wherein the sequenced genomic fragment encodes a tyrosine ammonia lyase enzyme.

Similarly the invention provides a method of obtaining a nucleic acid molecule encoding a tyrosine ammonia lyase enzyme comprising:
  a) synthesizing at least one oligonucleotide primer corresponding to a portion of the sequence as set forth in SEQ ID NO:2; and
  b) amplifying an insert present in a cloning vector using the oligonucleotide primer of step (a);

wherein the amplified insert encodes a portion of an amino acid sequence encoding a tyrosine ammonia lyase enzyme.

In a preferred embodiment the invention provides a method for the production of pHCA comprising:
  (a) contacting a recombinant host cell with a fermentable carbon substrate, said recombinant cell comprising the isolated nucleic acid molecule of the invention operably linked to suitable regulatory sequences;
  (b) growing said recombinant cell for a time sufficient to produce pHCA; and
  (c) optionally recovering said pHCA.

BRIEF DESCRIPTION OF THE FIGURES AND SEQUENCE DESCRIPTIONS

The invention can be more fully understood from the following detailed description, figures and the accompanying sequence descriptions, which form a part of this application.

FIG. 1 is a gel image of the SDS-polyacrylamide gel eletrophoresis analysis of RsTAL expression in *E.coli*.

FIG. 2 is a gel image of the SDS-polyacrylamide gel eletrophoresis analysis of the purified RsTAL enzyme.

The following sequences conform with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the amino acid sequence of the TAL from *T. cutaneum*.

SEQ ID NO:2 is the nucleotide sequence of the TAL gene from *Rhodobacter sphaeroides*.

SEQ ID NO:3 is the deduced amino acid sequence of the TAL from *Rhodobacter sphaeroides* encoded by the nucleotide sequence of SEQ ID NO:2.

SEQ ID NOs:4–7 are the oligonucleotide primers used for cloning of the *Rhodobacter sphaeroides* tal.

DETAILED DESCRIPTION OF THE INVENTION

The present invention provides a new DNA sequence that encodes an ammonia lyase enzyme from the bacterium *Rhodobacter sphaeroides*. This enzyme is only the second naturally occurring bacterial TAL enzyme reported with a higher specific activity when tyrosine is used as the substrate as opposed to phenylalanine. This TAL enzyme can be used for the production of pHCA directly from tyrosine.

Definitions

The following abbreviations and definitions will be used for the interpretation of the specification and the claims.

"Phenylalanine ammonia-lyase" is abbreviated PAL.

"Tyrosine ammonia-lyase" is abbreviated TAL.

"Histidine ammonia lyase" is abbreviated HAL.

"Para-hydroxycinnamic acid" is abbreviated pHCA.

"Cinnamate 4-hydroxylase" is abbreviated C4H.

As used herein the terms "cinnamic acid" and "cinnamate" are used interchangeably and are abbreviated CA.

The term "TAL activity" refers to the ability of a protein to catalyze the direct conversion of tyrosine to pHCA.

The term "PAL activity" refers to the ability of a protein to catalyze the conversion of phenylalanine to cinnamic acid.

"pal" represents a gene that encodes an enzyme with PAL activity.

"tal" represents a gene that encodes an enzyme with TAL activity.

"RsTAL" represents the TAL enzyme from *Rhodobacter sphaeroides*.

The term "P-450/P-450 reductase system" refers to a protein system responsible for the catalytic conversion of cinnamic acid to pHCA. The P-450/P-450 reductase system is one of several enzymes or enzyme systems known in the art that performs a cinnamate 4-hydroxylase function. As used herein the term "cinnamate 4-hydroxylase" will refer to the general enzymatic activity that results in the conversion of cinnamic acid to pHCA, whereas the term "P-450/P-450 reductase system" will refer to a specific binary protein system that has cinnamate 4-hydroxylase activity.

The term "PAL/TAL activity" or "PAL/TAL enzyme" refers to a protein which contains both PAL and TAL activity. Such a protein has at least some specificity for both tyrosine and phenylalanine as an enzymatic substrate.

The term "TAL/PAL ratio" means the ratio of TAL acitivity to PAL activity.

The term "catalytic efficiency" will be defined as the $k_{cat}/K_m$ of an enzyme. "Catalytic efficiency" will be used to quantify the specificity of an enzyme for a substrate.

The term "$k_{cat}$" is often called the "turnover number". The term "$k_{cat}$" is defined as the maximum number of substrate molecules converted to products per active site per unit time, or the number of times the enzyme turns over per unit time. $k_{cat}=V_{max}/[E]$, where [E] is the enzyme concentration (Ferst In *Enzyme Structure and Mechanism*, 2$^{nd}$ ed.; W. H. Freeman: New York, 1985; pp 98–120).

The term "aromatic amino acid biosynthesis" means the biological processes and enzymatic pathways internal to a cell needed for the production of an aromatic amino acid.

The term "fermentable carbon substrate" refers to a carbon source capable of being metabolized by host organisms of the present invention and particularly carbon sources selected from the group consisting of monosaccharides, oligosaccharides, polysaccharides, one-carbon substrates and/or mixtures thereof.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS is increased to 60° C. Another preferred set of highly stringent conditions uses two final washes in 0.1× SSC, 0.1% SDS at 65° C. An additional set of stringent conditions include hybridization at 0.1× SSC, 0.1% SDS, 65° C. and washed with 2× SSC, 0.1% SDS followed by 0.1× SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410. In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The invention encompasses more than the specific exemplary sequences because it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

Suitable nucleic acid fragments (isolated polynucleotides of the present invention) encode polypeptides that are at least about 70% identical, preferably at least about 80% identical to the amino acid sequence reported herein. Preferred nucleic acid fragments encode amino acid sequences that are about 85% identical to the amino acid sequence reported herein. More preferred nucleic acid fragments encode amino acid sequences that are at least about 90% identical to the amino acid sequence reported herein. Most preferred are nucleic acid fragments that encode amino acid sequences that are at least about 95% identical to the amino acid sequence reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptide as set forth in SEQ ID NO:3. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA.

In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to an RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Antisense inhibition" refers to the production of antisense RNA transcripts capable of suppressing the expression of the target protein.

"Overexpression" refers to the production of a gene product in transgenic organisms that exceeds levels of production in normal or non-transformed organisms.

"Co-suppression" refers to the production of sense RNA transcripts capable of suppressing the expression of identical or substantially similar foreign or endogenous genes (U.S. Pat. No. 5,231,020).

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, NY (1984); and by Ausubel, F. M. et al., *Current Protocols in Molecular Biology*, published by Greene Publishing Assoc. and Wiley-Interscience (1987).

Gene Involved in pHCA Production in *Rhodobacter sphaeroides*

The gene encoding the TAL activity of the present invention was identified and isolated from the bacterium *Rhodobacter sphaeroides*. Rhodobacter belong to a group of purple photosynthetic bacteria that contain photoactive yellow protein, which serves as a light sensor. pHCA is the chromophore for this photoactive yellow protein. The gene encoding this photoactive yellow protein has been isolated from *Rhodobacter sphaeroides* (Kort et al., *Biochim. Biophys. Acta* 1385:1–6 (1998)). It is believed that the TAL of Rhodobacter species catalyzes the production of pHCA directly from tyrosine. The pHCA is then activated by a specific ligase for binding to the photoactive yellow apoprotein (Kyndt et al., *FEBS Letters* 512:240–244 (2002)).

Sequence Identification

The nucleotide sequence identified in *Rhodobacter sphaeroides* that encodes the TAL enzyme of this invention is given as SEQ ID NO:2. Comparison of this nucleotide and the deduced amino acid (SEQ ID NO:3) sequences to public databases reveals that the most similar known sequences are about 56% identical to the amino acid sequence reported herein over a length of 526 amino acids using a Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). More preferred amino acid fragments are at least about 70%–80% identical to the sequences herein, where about 80%–90% is preferred. Most preferred are amino acid fragments that are at least 95% identical to the amino acid fragments reported herein. Similarly, preferred TAL encoding nucleic acid sequences corresponding to the instant sequence are those encoding active proteins and which are at least 80% identical to the nucleic acid sequence reported herein. More preferred tat nucleic acid fragments are at least 90% identical to the sequence herein. Most preferred are tat nucleic acid fragments that are at least 95% identical to the nucleic acid fragment reported herein.

Isolation of Homologs

The nucleic acid fragment of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Natl. Acad. Sci. USA* 82, 1074, (1985); or strand displacement amplification (SDA), Walker, et al., *Proc. Natl. Acad. Sci. U.S.A.,* 89: 392, (1992)).

For example, genes encoding similar proteins or polypeptides to those of the instant invention could be isolated directly by using all or a portion of the instant nucleic acid fragment as DNA hybridization probes to screen libraries from any desired bacteria using methodology well known to those skilled in the art. Specific oligonucleotide probes based upon the instant nucleic acid sequence can be designed and synthesized by methods known in the art (Maniatis, supra). Moreover, the entire sequence can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or the full-length of the instant sequence. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally two short segments of the instant sequence may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragment, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *Proc. Nat. Acad. Sci. USA* 85:8998 (1988)) to generate cDNAs by using PCR to amplify copies of the region between a single point in the transcript and the 3' or 5' end. Primers oriented in the 3' and 5' directions can be designed from the instant sequence. Using commercially available 3' RACE or 5' RACE systems (Life Technologies, Rockville, Md.), specific 3' or 5' cDNA fragments can be isolated (Ohara et al., *Proc. Natl. Acad. Sci. USA* 86:5673 (1989); Loh et al., *Science* 243:217 (1989)).

Alternatively the instant sequence may be employed as an hybridization reagent for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151(1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons (kD)), polyvinylpyrrolidone (about 250–500 kD), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Recombinant Expression—Microbial

The gene and gene product of the instant sequence may be produced in heterologous host cells, particularly in the cells of microbial hosts.

Microbial expression systems and expression vectors containing regulatory sequences that direct high level expression of foreign proteins are well known to those skilled in the art. Any of these could be used to construct chimeric genes for production of the gene product of the instant sequence. These chimeric genes could then be introduced into appropriate microorganisms via transformation to provide high level expression of the enzyme.

Accordingly, it is expected for example that introduction of a chimeric gene encoding the instant microbial enzyme under the control of the appropriate promoters will demonstrate increased production of pHCA. It is contemplated that it will be useful to express the instant gene both in natural host cells as well as heterologous hosts. Introduction of the present gene into the native host will result in elevated levels of existing production of pHCA. Additionally, the instant gene may also be introduced into non-native host bacteria where there are advantages to manipulate the pHCA production that are not present in the organism from which the instant gene is directly isolated.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the instant TAL gene in the desired host cell are numerous and familiar to those skilled in the art. Virtually any promoter capable of driving this gene is suitable for the present invention including, but not limited to: CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, ara, tet, trp, $IP_L$, $IP_R$, T7, tac, and trc (useful for expression in *Escherichia coli*) as well as the amy, apr, npr promoters and various phage promoters useful for expression in Bacillus.

Termination control regions may also be derived from various genes native to the preferred hosts. Optionally, a termination site may be unnecessary; however, it is most preferred if included.

Preferred heterologous host cells for expression of the instant gene and nucleic acid fragment are microbial hosts that can be found broadly within the fungal or bacterial families and which grow over a wide range of temperature, pH values, and solvent tolerances. For example, it is contemplated that any bacteria, yeast, and filamentous fungi will be suitable hosts for expression of the present nucleic acid fragment. Because transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and/or saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of host strains include but are not limited to bacteria, such as the enteric bacteria (Escherichia, and Salmonella for example) as well as Bacillus, Acinetobacter, Streptomyces, Methylobacter, and Pseudomona; Cyanobacteria, such as Rhodobacter and Synechocystis; yeasts, such as Saccharomyces, Zygosaccharomyces, Kluyveromyces, Candida, Hansenula, Debaryomyces, Mucor, Pichia and Torulopsis; filamentous fungi such as Aspergillus and Arthrobotrys; and algae such Spirulina, Haemotacoccus, and Dunalliela. The TAL gene of the present invention may be produced in these and other microbial hosts to prepare large, commercially useful amounts of pHCA.

Pathway Engineering

Knowledge of the sequence of the TAL gene will be useful in manipulating the pHCA biosynthetic pathways in any organism having such a pathway. Moreover, introducing the TAL gene into any organism with the endogenous or engineered ability to produce tyrosine will enable PCHA production from a carbon source such as glucose. Methods of manipulating genetic pathways are common and well known in the art. Selected genes in a particularly pathway may be upregulated or down regulated by variety of methods. Additionally, competing pathways in an organism may be eliminated or sublimated by gene disruption and similar techniques.

Once a key genetic pathway has been identified and sequenced, specific genes may be upregulated to increase the output of the pathway. For example, additional copies of the targeted gene may be introduced into the host cell on multicopy plasmids such as pBR322. Alternatively the target gene may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565, 350; Zarling et al., PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods for gene down regulation is targeted gene disruption where foreign DNA is inserted into a structural gene so as to disrupt transcription. This can be effected by the creation of genetic cassettes comprising the DNA to be inserted (often a genetic marker) flanked by sequences having a high degree of homology to a portion of the gene to be disrupted. Introduction of the cassette into the host cell results in insertion of the foreign DNA into the structural gene via the native DNA replication mechanisms of the cell. (See for example Hamilton et al. *J. Bacteriol.* 171:4617–4622 (1989); Balbas et al. *Gene* 136:211–213 (1993); Gueldener et al. *Nucleic Acids Res.* 24:2519–2524 (1996); and Smith et al. *Methods Mol. Cell. Biol.* 5:270–277(1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36: 227 (1992).

Another non-specific method of gene disruption is the use of transposable elements or transposons. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the EZ::TN Transposon Insertion Systems, available from Epicentre Technologies, Madison, Wis, based upon the Tn5 bacterial transposable element).

Within the context of the present invention, it may be useful to modulate the expression of the pHCA producing enzyme pathway by any one of the methods described above. For example, it would be advantageous to maximize the production of tyrosine from glucose by down-regulating competing pathways, such as the production of phenylalanine.

Industrial Production

Where commercial production of pHCA is desired, a variety of culture methodologies may be applied. For example, large-scale production of a specific gene product overexpressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted.

If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of pHCA may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products, or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof, and unpurified mixtures from renewable feedstocks such as cheese whey permeate, cornsteep liquor, sugar beet molasses, and barley malt. Additionally the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of Candida will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

Recombinant Expression—Plants

Alternatively, the present invention provides for the production of pHCA in plant cells containing the TAL gene. The nucleic acid fragment of the instant invention may be used to create transgenic plants having the ability to express the microbial gene for the production of pHCA. Preferred plant hosts will be any variety that will support a high production level of pHCA or pHCA-glucoside conjugate. Suitable green plants will include, but are not limited to: soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum sp*), barley (*Hordeum vulgare*), oats (*Avena sativa*, L), sorghum (*Sorghum bicolor*), rice (*Oryza sativa*), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Overexpression of the pHCA may be accomplished by first constructing a chimeric gene of the present invention in which the coding regions are operably linked to promoters capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals must also be provided. The instant chimeric gene may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequence or the present invention should be capable of promoting expression of the present gene product. High level plant promoters that may be used in this invention, for example, include the promoter of the small subunit (ss) of the ribulose-1,5-bisphosphate carboxylase from soybean (Berry-Lowe et al., *Journal of Molecular and Applied Genetics*, 1:483–498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pp 29–38; Coruzzi, G. et al., *J. Biol. Chem.*, 258:1399 (1983), and Dunsmuir, P. et al., *Journal of Molecular and Applied Genetics*, 2:285 (1983)).

Plasmid vectors comprising the instant chimeric gene can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus multiple events must be screened in order to obtain lines displaying the desired expression level and pattern. Such screening may be accomplished by Southern analysis of DNA blots (Southern, *J. Mol. Biol.* 98, 503, (1975)), Northern analysis of mRNA expression (Kroczek, *J. Chromatogr. Biomed. Appl.*, 618 (1–2) 133–145 (1993)), Western analysis of protein expression, or phenotypic analysis.

For some applications it will be useful to direct the instant protein to different cellular compartments. It is thus envisioned that the chimeric gene described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.*100: 1627–1632 (1992)) added and/or with targeting sequences that are already present removed. While the references cited give examples of each of these, the list is not exhaustive and more targeting signals of utility may be discovered in the future that are useful in the invention.

Protein Engineering

It is contemplated that the present nucleotide may be used to produce gene products having enhanced or altered activity. Various methods are known for mutating a native gene sequence to produce a gene product with altered or enhanced activity including but not limited to error prone PCR (Melnikov et al., *Nucleic Acids Research* 27(4):1056–1062 (1999)); site directed mutagenesis (Coombs et al., *Proteins* (1998), 259–311, 1 plate, Editor(s): Angeletti, Ruth Hogue, Publisher: Academic, San Diego, Calif.), and "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequence of the present invention may be mutated and screened for altered or enhanced activity by this method. The sequences should be double stranded and can be of various lengths ranging from 50 bp to 10 kb. The sequences may be randomly digested into fragments ranging from about 10 bp to 1000 bp, using restriction endonucleases well known in the art (Maniatis, supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocols (Manatis, supra).

Furthermore, a hybrid protein can be assembled by fusion of functional domains using the gene shuffling (exon shuffling) method (Nixon et al., *Proc. Natl. Acad. Sci. USA* 94:1069–1073 (1997)). The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

Description of Preferred Embodiments

The present invention provides an enzyme which can be used for the production of pHCA directly from tyrosine. The instant gene of this invention encodes a protein having tyrosine ammonium lyase (TAL) activity. A TAL activity will convert tyrosine directly to pHCA with no intermediate step according to the following scheme:

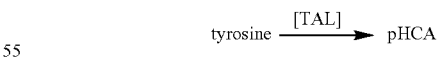

The TAL gene of the instant invention was identified by using the amino acid sequence of the TAL, which was isolated from *Trichosporon cutaneum* (SEQ ID NO:1) (Sariaslani et al., U.S. Patent Application Ser. No. 60/383232), to search the available translated genomic sequence of *Rhodobacter sphaeroides* from the ongoing *Rhodobacter sphaeroides* genome sequencing project. Two open reading frames (ORFs) were found with high homology with the *T. cutaneum* TAL sequence. One of these ORFs was found to be more closely related to the recently identified TAL from *Rhodobacter capsulatus* (Kyndt et al., *FEBS Letters* 512:

240–244 (2002)), and therefore, was concluded to be a TAL gene. The TAL protein sequence of the instant invention (SEQ ID NO:3) had a 56% identity with the protein sequence of the TAL from *Rhodobacter capsulatis*. The TAL gene was cloned using direct PCR amplification of the genomic DNA as template and was expressed in *E. coli*. Following expression in *E. coli*, the RsTAL enzyme was purified using perfusion chromatography and characterized using kinetic analysis. The RsTAL was found to have a TAL/PAL ratio of 19, indicating that it has a significantly higher activity with tyrosine as a substrate than with phenylalanine.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth, and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "M" means molar, "mmol" means millimole(s), "μmole" means micromole(s)", "g" means gram(s), "μg" means microgram(s) and "ng" means nanogram(s), "U" means units, "mU" means milliunits and "U mg$^{-1}$" means units per mg, "OD" means optical density, "OD$_{600}$" means the optical density measured at a wavelength of 600 nm, "ppm" means parts per million, "kD" means kilodaltons, "rpm" means revolutions per minute.

Example 1

Identification of a TAL Gene in *Rhodobacter sphaeroides*

The purpose of this Example was to identify genes of *Rhodobacter sphaeroides* that encode a tyrosine ammonia lyase enzyme.

Blast Analysis

The amino acid sequence of the TAL from *Trichosporon cutaneum*, given as SEQ ID NO:1 (Sariaslani et al., U.S. Patent Application Ser. No. 60/383232), was used to search the translated genomic sequence of *Rhodobacter sphaeroides* from the ongoing *Rhodobacter sphaeroides* genome sequencing project.

The Blast results revealed that there are currently two open reading frames (ORFs) that share significant homology with the TAL sequence. One of the sequences is on Contig 204, which has an Expect (E) value of 2e-46 when compared with the *T. cutaneum* TAL sequence. The Expect value estimates the statistical significance of the match, specifying the number of matches, with a given score, that are expected in a search of a database of this size absolutely by chance. The second sequence is on Contig 230 which has an E value of 4e-42 when compared with the *T. cutaneum* TAL sequence. Comparison with the sequences of a number of phenylalanine, tyrosine and histidine ammonia lyases showed that the ORF on Contig 204 is most closely related to histidine ammonia lyase, whereas the ORF on Contig 230 is more closely related to the recently identified tyrosine ammonia lyase from Rhodobacter capsulatus (Kyndt et al, *FEBS Letters* 512:240–244 (2002)). Therefore, we concluded that this latter ORF is a TAL gene. The DNA sequence of this TAL gene is given as SEQ ID NO:2. This sequence includes the entire coding region plus 146 bases of the 5' flanking region and 123 bases of the 3' flanking region. The translated protein sequence of this *Rhodobacter sphaeroides* TAL (RsTAL), designated as SEQ ID NO:3, is 526 amino acids long.

The amino acid sequence obtained for the *Rhodobacter sphaeroides* TAL (SEQ ID NO:3) was analyzed for similarity to all publicly available protein sequences by conducting a BLAST (Basic Local Alignment Search Tool; Altschul, S. F., et al., (1993) *J. Mol. Biol.* 215:403–410; search for similarity to sequences contained in the BLAST "p" database (comprising all non-redundant GenBank CDS translations, sequences derived from the 3-dimensional structure Brookhaven Protein Data Bank, the SWISS-PROT protein sequence database, EMBL, and DDBJ databases) using the BLASTN algorithm provided by the National Center for Biotechnology Information (NCBI). The TAL amino acid sequence from *T. cutaneum* was also included for comparison.

The results of the BLAST comparison are given in Table 1, which displays data based on the BLASTXp algorithm with values reported in Expect values. The results show that the TAL from *Rhodobacter sphaeroides* has a high degree of similarity to other TAL, PAL and HAL enzymes. The TAL from *Rhodobacter sphaeroides* and *Rhodobacter capsulatus* have a 56% identity at the amino acid level.

TABLE 1

BLAST Comparison of TAL from *Rhodobacter sphaeroides* (SEQ ID NO: 3)

| GENE | SIMILARITY IDENTIFIED | % IDENTITY[A] | % SIMILARITY[B] | E-VALUE[C] | CITATION |
|---|---|---|---|---|---|
| TAL [*R. sphaeroides*] | TAL [*R. capsulatus*] | 56 | 65 | e−133 | Kyndt, et al., FEBS Letters 512, 240–244 (2002) |
| | HAL [*T. tengcongensis*] | 35 | 53 | e−71 | Bao, et al., Genome Res. 12 (5), 689–700 (2002) |
| | PAL [*S. maritimus*] | 33 | 50 | e−68 | Piel, et al., J. Am. Chem. Soc. 122, 5415–5416 (2000) |
| | TAL [*T. cutaneum*] | 30 | 45 | e−46 | Sariaslani, et al., U.S. patent application No. 60/383232 |
| | HAL [*F. nucleatum*] | 35 | 52 | e−65 | Kapatral, et al. J. Bacterial. 184 (7), 2005–2018 (2002) |
| | PAL [*B. finlaysoniana*] | 30 | 48 | e−44 | Liew, et al., unpublished |

[A]% Identity is defined as percentage of amino acids that are identical between the two proteins.
[B]% Similarity is defined as percentage of amino acids that are identical or conserved between the two proteins.
[C]Expect value. The Expect value estimates the statistical significance of the match, specifying the number of matches, with a given score, that are expected in a search of s database of this size absolutely by chance.
% Identity, % Similarity, and E-values are all reported according to FASTA analysis with Smith-Waterman computation.

Example 2

Expression of the TAL Gene from *Rhodobacter sphaeroides* in *E. coli*

The purpose of this example was to clone the gene encoding the TAL enzyme from *Rhodobacter sphaeroides* and express it in *E. coli* to confirm its activity and to characterize it.

Based on the DNA sequence of the TAL gene identified from the *Rhodobacter sphaeroides* sequencing project, the primers listed in Table 2 were designed for PCR cloning by direct PCR amplification using genomic DNA as template. Rhodobacter sphaeroides genomic DNA was purchased from The American Type Culture Collection (Manassas, Va.) and was diluted 10-fold in water before use. The coding region of the TAL gene was amplified by PCR and cloned into pKK223-3 or pTricHisTOPO® vectors (Invitrogen, Carlsbad, Calif.).

TABLE 2

Primers for Cloning the TAL Gene from *Rhodobacter sphaeroidesp*

| Name | Sequence (5'-3') | SEQ ID NO: |
|---|---|---|
| RS-TAL-F | GATCCCCGGGGTGAAGCCAATGCTCGCCAT | 4 |
| RS-TAL-R | GATCAAGCTTCGATCGAGACCTGGCTCAAA | 5 |
| RS-TAL-F1 | ATGAAGCCAATGCTCGCCAT | 6 |

For the vector pKK223-3, primers RS-TAL-F and RS-TAL-R (SEQ ID NOs: 4 and 5) were used to amplify the coding region of the *Rhodobacter sphaeroides* tal, starting at the GTG start codon and ending 73 base pairs after the stop codon. The PCR reaction mixture contained 1 μL of *Rhodobacter sphaeroides* genomic DNA (1:10 dilution), 1 μL each of the two primers (at 20 μM), 10 μL of 10× PCR buffer (ClonTech, Palo Alto, Calif.), 10 μL of 5 M G-C melt (ClonTech), 8 μL of 2.5 mM dNTP, 18 μL of H₂O, and 1 μL of Advantage G-C polymerase mix (ClonTech). The reaction mixture was heated to 94° C. for 2.5 min, then cycled as follows: 30 cycles of 30 s at 94° C., 30 s at 55° C., and 2 min at 72° C. These cycles were followed by a 7 min incubation at 72° C.

The PCR product (1674 base pair total length) was purified using the QIAquick PCR purification kit (Qiagen, Inc., Valencia, Calif.) according to the manufacturer's protocol. Purified PCR product and vector pKK223-3 were digested separately with SmaI. The reaction mixtures contained 50 μL of PCR product (~15 μg of DNA) or 50 μL pKK223-3 (~10 μg), 10 μL NE Buffer 4 (New England BioLabs, Beverly, Mass.), 36 μL water and 4 μL SmaI (20 units/μL, New England Biolabs, Beverly, Mass.). After incubation for 4 h at room temperature, the digested DNA samples were purified with the QIAquick PCR purification kit. The DNA samples were then digested with HindIII. The reaction mixtures contained 50 μL SmaI-digested DNA (~15 μg for the PCR product or 10 μg for pKK223-3), 10 μL NE Buffer 2 (New England BioLabs), 4 μL HindIII (20 units/μL, New England BioLabs) and 36 μL water. The reaction mixtures were incubated at 37° C. for 4 h. Digested DNA samples were purified again with the QIAquick PCR purification kit. The PCR product was then ligated with the vector using T4 ligase. The reaction mixture contained 2 μL each of digested pKK223-3 and the PCR product, 2 μL 10× ligase buffer (New England BioLabs), 13 μL water and 1 μL T4 ligase (New England BioLabs). After incubation overnight at room temperature, the ligation mixture was used to transform Top10 *E. coli* competent cells (Invitrogen, Carlsbad, Calif.). Transformed cells were plated on an LB plate consisting of 1% Bacto-Tryptone, 0.5% Bacto-Yeast Extract, 0.5% NaCl, 1 mM NaOH and 2% Bacto-agar, supplemented with 100 μg/mL ampicillin.

Fifteen colonies from the transformation plate were used to inoculate separate 2 mL portions of LB liquid culture medium consisting of 1% Bacto-Tryptone, 0.5% Bacto-Yeast Extract, 0.5% NaCl, 1 mM NaOH and 100 μg/mL ampicillin. These cultures were incubated overnight. Plasmid DNA was purified from these cultures using a Qiagen Miniprep kit, following the manufacturer's protocol. Restriction digestion with EcoRI showed that 6 out of the 15 plasmids contained the tal insert.

For the vector pTricHis2-TOPO®, primers RS-TAL-F1 and RS-TAL-R (SEQ ID NOs: 6 and 5) were used to amplify a 1664 base pair DNA fragment. The reaction mixture contained 1 µL of *Rhodobacter sphaeroides* genomic DNA (1:10 dilution), 1 µL each of the two primers (at 20 µM), 10 µL of 10× PCR buffer, 10 µL of 5 M G-C melt, 8 µL of 2.5 mM dNTP, 18 µL of H₂O, and 1 µL of Advantage G-C polymerase mix (ClonTech). The reaction mixture was heated to 94° C. for 2.5 min, then cycled as follows: 30 cycles of 30 s at 94° C., 30 s at 55° C., and 2 min at 72° C. These cycles were followed by a 7 min incubation at 72° C.

The PCR product was purified with the QIAquick PCR purification kit (Qiagen, Inc) and directly ligated into pTricHis2-TOPO® cloning vector (Invitrogen). The reaction mixture contained 1 µL of the purified PCR product, 1 µL salt solution from the TOPO® cloning kit, 3 µL water and 1 µL TOPO® cloning vector mix. After a 10 minute incubation at room temperature, the ligation mix was used to transform Top10 *E. coli* competent cells. Transformation mix was plated on an LB plate containing 100 mg/mL ampicillin.

Fifteen colonies from the transformation plate were used to inoculate separate 2 mL portions of LB liquid culture medium consisting of 1% Bacto-Tryptone, 0.5% Bacto-Yeast Extract, 0.5% NaCl, 1 mM NaOH and 100 µg/mL ampicillin. These cultures were incubated overnight. Plasmid DNA was purified from these cultures using a Qiagen Miniprep kit, following the manufacturer's protocol. Restriction digestion with EcoRI showed that 6 out of the 15 plasmids contained the tal insert.

The 12 correct clones were used to inoculate separate 2 mL portions of LB liquid culture medium consisting of 1% Bacto-Tryptone, 0.5% Bacto-Yeast Extract, 0.5% NaCl, 1 mM NaOH and 100 µg/mL ampicillin. These cultures were incubated overnight at 37° C. and centrifuged at 14,000 rpm using an Eppendorf Microfuge (Brinkmann Instruments, Westbury, N.Y.). The supernatant from each culture was acidified with phosphoric acid, filtered through a 0.45 micron filter and analyzed by High Performance Liquid Chromatography (HPLC) to determine the concentration of pHCA and CA in the growth medium.

A Hewlett Packard Model 1090L HPLC system with an auto sampler and a diode array UV/vis detector was used with a reverse-phase Zorbax SB-C8 column (4.6 mm×250 mm), supplied by MAC-MOD Analytical Inc. (Chadds Ford, Pa.). A flow rate of 1.0 mL per min was used with Solvent A (methanol) and Solvent B (0.2% trifluoroacetic acid (TFA) in water) with the solvent gradient given in Table 3. The column temperature was maintained at 40° C. The UV detector was set to monitor the eluant at 250, 230, 270, 290 and 310 nm wavelengths.

TABLE 3

Solvent Gradient for HPLC Determination of pHCA and CA

| Time (min) | Solvent A Methanol | Solvent B 0.2% TFA |
|---|---|---|
| 0.0 | 10% | 90% |
| 0.1 | 10% | 90% |
| 9.0 | 35% | 65% |
| 9.1 | 50% | 50% |
| 14.0 | 50% | 50% |
| 18.0 | 100% | 0% |
| 21.0 | 100% | 0% |

As shown in Table 4, three of the pTricHis2 based clones produced significant levels of pHCA. In addition, two of the pKK223-3 based clones also produced low but detectable amounts of pHCA. The level of CA produced in all cases was negligible. These results demonstrate that the enzyme encoded by SEQ ID NO:2 is indeed a TAL. The reason that some clones didn't produce any pHCA could be due to mutations created by PCR, or due to a lack of expression under the non-inducing condition used in the experiment.

TABLE 4 pHCA and CA Levels in *E. coli* Cultures

| Clone | pHCA (ppm) | CA (ppm) |
|---|---|---|
| 1 pRsTAL-KK223 No. 1 | 0.59 | 0 |
| 2 pRsTAL-KK223 No. 2 | 0.77 | 0 |
| 3 pRsTAL-KK223 No. 3 | 3.78 | 0 |
| 4 pRsTAL-KK223 No. 4 | 0 | 0 |
| 5 pRsTAL-KK223 No. 5 | 2.60 | 0 |
| 6 pRsTAL-KK223 No. 6 | 0 | 0 |
| 7 pKK223-3 | 0.36 | 0 |
| 8 pRsTAL-TricHis2 No. 1 | 23.5 | 1 |
| 9 pRsTAL-TricHis2 No. 2 | 0 | 0 |
| 10 pRsTAL-TricHis2 No. 3 | 0.72 | 0 |
| 11 pRsTAL-TricHis2 No. 4 | 22.72 | 0.9 |
| 12 pRsTAL-TricHis2 No. 5 | 0 | 0 |
| 13 pRsTAL-TricHis2 No. 6 | 4.63 | 0 |
| 14 pTricHis2 | 0 | 0 |

Example 3

Expression. Purification, and Kinetic Studies of the *Rhodobacter sphaeroides* TAL Enzyme (RsTAL)

The purpose of this example was to clone the gene encoding the TAL enzyme from *Rhodobacter sphaeroides* into a medium copy expression vector for the overexpression, purification, and kinetic characterization of the RsTAL.

Expression of RsTAL in *E. coli*

The medium copy expression vector pKK233.RsTAL2, containing a strong Ptrc promoter for the high level expression of RsTAL protein, was prepared as follows. The TAL gene was amplified from *Rhodobacter sphaeroides* genomic DNA by PCR using the primer given as SEQ ID NO:7 and the RS-TAL-R primer (described in Example 2), given as SEQ ID NO:5, and ligated into the vector pKK233-2 (Amersham Pharmacia Biotech, Piscataway, N.J.), which was digested with NcoI and HindIII restriction enzymes, to give pKK233.RsTAL2. Expression of RsTAL was carried out in *E. coli* BL21(DE3)RP codon plus strain (Stratagene, San Diego, Calif.) transformed with pKK233.RsTAL2. The transformed cells, designated as *E. coli* BL21(DE3)RP (pKK233.RsTAL2), were inoculated into LB media containing 100 µg/mL of ampicillin, grown to mid log phase (OD$_{600}$=0.4), induced by 1 mM IPTG (isopropyl β-D-thioglucopyranoside), and incubated overnight (18 h) in a 37° C. shaker. The culture supernatants were analyzed by HPLC for pHCA formation, as described in Example 2. These results are given in Table 5.

Crude cell extracts were generated by sonication of a suspension of the transformed cells, followed by centrifugation. The TAL enzyme activity of the crude cell extracts was determined by an enzyme assay using 40 µg of crude cell extract in 10 mM Tris-HCl, pH 8.5 buffer containing 1 mM tyrosine. The OD of the pHCA produced was followed at 315 nm with an extinction coefficient of 10,000 cm$^{-1}$. The results of the TAL enzyme assay are given in Table 5 in terms of activity units. A unit (U) is defined as follows: one unit of activity deaminated 1 µmol of tyrosine to pHCA per min. The results shown in Table 5 demonstrate the successful expression of the RsTAL enzyme in *E. coli*.

TABLE 5

Results of the HPLC Analysis of pHCA Formation and the TAL Enzyme Assay of TAL from *E. coli* BL21(DE3)RP(pKK233.RsTAL2)

| Induction | CA (ppm) | pHCA (ppm) | TAL Activity (mU/40 µg extract) |
|---|---|---|---|
| No IPTG | 3.9 | 49 | 0.23 |
| 1 mM IPTG | 3.1 | 45 | 0.33 |

Both the soluble and insoluble fractions of the crude cell extracts were analyzed by SDS-polyacrylamide gel electrophoresis (SDS-PAGE). The expression of RsTAL, as indicated by a band corresponding to a molecular weight of about 55 kD, was detected in both the soluble and insoluble fractions, as shown in FIG. 1. In the figure, lanes 1 and 2 represent the insoluble fraction, without (−) and with (+) IPTG induction, respectively. Lanes 3 and 4 represent the soluble fraction, without (−) and with (+) IPTG induction, respectively. The first lane on the left in the FIG. is the Mark12™ molecular weight standard, obtained from Invitrogen Corp. (Carlsbad, Calif.).

Purification and Kinetic Analysis of RsTAL

A 500 mL culture of the *E. coli* BL21(DE3)RP (pKK233.RsTAL2) strain was grown in LB Broth, containing 100 mg/mL ampicillin to mid log phase, induced with 1 mM IPTG, and incubated overnight (18 h) in a 37° C. shaker. The cells were centrifuged and resuspended in 10 mL of Buffer A (50 mM Tris-HCl, pH 8.5 buffer, 5 mM DTT (dithiothreitol), and 1 mM tyrosine) containing one and a half EDTA-free protease inhibitor tablets (Roche Applied Science, Indianapolis, Ind.). The cells were then passed through a French Press Cell twice, and centrifuged at 18000 rpm for 20 min. Ammonium sulfate at 30% saturation was added to the culture supernatant and the resulting precipitate was removed by centrifugation. The supernatant from this first fractionation was then treated with ammonium sulfate at 50% saturation. The pellet from the second ammonium sulfate fractionation was re-dissolved in 3 mL of Buffer A, and the resulting solution was loaded onto an HQ anion exchange perfusion chromatography column (Applied Biosystems, Foster city, Calif.). The column was washed with 10 mL of Buffer A, and eluted with Buffer A containing a gradient of 0 to 1 M NaCl. The eluted fractions were analyzed for TAL activity, and the fractions containing TAL activity were pooled, precipitated again using ammonium sulfate at 50% saturation, and desalted using a 3 mL desalting column (Bio-Rad Laboratories, Hercules, Calif.). The desalted protein sample was purified further by HQ perfusion chromatography, as described above. TAL activity was detected in the flow-through fractions. These fractions contained purified RsTAL protein near homogeneity, as shown by the SDS-PAGE results given in FIG. 2. In this figure, lane 1 is the Mark12™ molecular weight standard and lane 2 is the purified RsTAL protein.

The kinetic parameters of the RsTAL enzyme were characterized using the TAL enzyme assay described above. The initial rates of the enzyme reaction were measured at tyrosine concentrations of 0.01 to 10 mM in 50 mM Tris-HCl, pH 8.5 buffer. The values of $k_{cat}$ and $K_m$ of the RsTAL enzyme for both tyrosine and phenylalanine were determined using Lineweaver-Burk analysis and the results are given in Table 6.

TABLE 6

Kinetic Parameters of the RsTAL Enzyme

| Substrate | $K_m$ (µM) | $k_{cat}$ (s$^{-1}$) | $k_{cat}/K_m$ (M$^{-1}$s$^{-1}$) | TAL/PAL Ratio |
|---|---|---|---|---|
| Tyrosine | 60 | 0.02 | 333 | 19 |
| Phenylalanine | 560 | 0.01 | 18 | |

As can be seen from the data in Table 6, the RsTAL enzyme has a TAL/PAL ratio of 19, indicating that it has a significantly higher activity with tyrosine as a substrate than with phenylalanine.

What is claimed is:

1. An isolated nucleic acid molecule encoding a tyrosine ammonia lyase enzyme, selected from the group consisting of:
   a) an isolated nucleic acid molecule encoding the amino acid sequence as set forth in SEQ ID NO:3;
   b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or an isolated nucleic acid molecule that is complementary to (a) or (b).

2. An isolated nucleic acid molecule as set forth in SEQ ID NO:2.

3. An isolated nucleic acid molecule comprising a first nucleotide sequence encoding a polypeptide of at least 526 amino acids that has at least 95% identity based on to Smith-Waterman method of alignment when compared to a polypeptide having the sequence as set forth in SEQ ID NO:3 or a second nucleotide sequence comprising the complement of the first nucleotide sequence, wherein said polpeptide has tyrosine ammonia lyase activity.

4. A chimeric gene comprising the isolated nucleic acid molecule of claims 1 or 2 operably linked to suitable regulatory sequences.

5. A transformed host cell comprising the chimeric gene of claim 4.

6. The transformed host cell of claim 5 wherein the host cell is selected from the group consisting of bacteria, yeast, filamentous fungi, algae, and green plants.

7. The transformed host cell of claim 6 wherein the host cell is selected from the group consisting of *Escherichia, Salmonella, Bacillus, Acinetobacter, Streptomyces, Methylobacter, Rhodococcus, Pseudomonas, Rhodobacter, Synechocystis, Aspergillus* and *Arthrobotrys*.

8. The transformed host cell of claim 5 wherein the host cell is selected from the group consisting of *Saccharomyces, Zygosaccharomyces, Kluyveromyces, Candida, Hansenula, Debaryomyces, Pichia, Mucor*, and *Torulopsis*.

9. The transformed host cell of claim 5 wherein the host cell is selected from the group consisting of soybean, rapeseed, pepper, sunflower, cotton, corn, tobacco, alfalfa, wheat barley, oats, sorghum, rice, *Arabidopsis*, cruciferous vegetables, melons, carrots, celery, parsley, tomatoes, potatoes, strawberries, peanuts, grapes, grass seed crops, sugar beets, sugar cane, beans, peas, rye, flax, hardwood frees, softwood trees, and forage grasses.

* * * * *